United States Patent [19]

Reinhold, Jr.

[11] 4,060,079

[45] Nov. 29, 1977

[54] HEART-LUNG RESUSCITATOR LITTER UNIT

[75] Inventor: Herbert E. Reinhold, Jr., Rockville, Md.

[73] Assignee: Survival Technology, Inc., Bethesda, Md.

[21] Appl. No.: 632,657

[22] Filed: Nov. 17, 1975

[51] Int. Cl.$^{2}$ .............................................. A61M 16/00

[52] U.S. Cl. ................................ 128/145.8; 128/30.2; 128/376; 128/1 R; 269/322; 5/82 R

[58] Field of Search ............... 128/145.8, 145.5, 145.6, 128/30.2, 28, 1 R, 188, 376; 269/322-328; 5/82 R; 296/20 R

[56] References Cited

U.S. PATENT DOCUMENTS

| | | | |
|---|---|---|---|
| 1,924,496 | 8/1933 | Herod | 296/20 |
| 2,517,443 | 8/1950 | Rhodes et al. | 296/20 |
| 2,675,564 | 4/1954 | Hughes | 5/82 |
| 3,461,858 | 8/1969 | Michelson | 128/28 |
| 3,838,687 | 10/1974 | Mosher | 128/188 |
| 3,886,606 | 6/1975 | Bradford | 5/82 |
| 3,889,663 | 6/1975 | Fryer | 128/28 |

OTHER PUBLICATIONS

Travenol Laboratories, Inc., "When Heart Attack Strikes," Oct., 1973.

*Primary Examiner*—Robert W. Michell
*Assistant Examiner*—Henry J. Recla
*Attorney, Agent, or Firm*—Cushman, Darby & Cushman

[57] ABSTRACT

A device for use under emergency conditions in applying heart-lung resuscitation procedures and the like to a patient while supported thereon which enables such patient to be transported from an inaccessible location of attack onto an ambulance stretcher without removing such support, the device being in the form of a self-contained portable unit comprising a frame structure having parts relatively movable between a collapsed unit carrying position and an extended patient supporting treatment and a transporting position operable when disposed in the patient treatment and transporting position to be engaged on a horizontal surface such as a floor or the like for support in stable relation thereon and to engage and support a patient thereon in a supine position to provide for a relatively unyielding support of the patient's back area sufficient to effect cardiac compression through the application of periodic mechanical downward forces on the chest area of the patient. A heart-lung resuscitator assembly is carried by the frame structure for applying periodic mechanical downward forces on the chest area of the patient, the assembly being contoured adjacent the head end of the frame structure to support the head of the patient in a position extending downwardly from the adjacent back area so that the breathing channel is maintained in a favorable position for the reception of oxygen and including a face mask unit engageable with the face of a patient supported as aforesaid for supplying oxygen to the patient. A drug and equipment compartment assembly is provided on the frame structure for supporting containers of oxygen thereon for use with the resuscitator assembly.

8 Claims, 8 Drawing Figures

HEART-LUNG RESUSCITATOR LITTER UNIT

This invention relates to emergency patient care and more particularly to improved equipment used in emergency patient care having heart and lung resuscitation capabilities.

Emergency patient care of the type herein contemplated is that dispensed by ambulance and rescue squad crews, police and fire departments and by special crews in large industrial installations and the like.

It is customary for those skilled in this art to refer to a wheeled device for supporting a patient in a horizontal transporting position as a stretcher. The term stretcher as herein used contemplates this accepted usage which does not comprehend within its meaning different devices for performing the patient transportation function which do not have the capability of supporting the patient for movement along a horizontal supporting surface. Devices in which the patient transportation function must be performed by two individuals carrying the device and patient are known as litter devices or litters.

Stretchers have long been a standard adjunct to ambulance vehicles. So-called "ambulance stretchers" have become generally standardized in their dimensions. In recent years ambulance stretchers have been equipped with permanentaly attached treatment equipment such as heart-lung resuscitating devices, heart monitoring and ECG recording devices, defibrilating devices and the like. These stretcher systems have served to extend these treatment capabilities to the patient at the location where stricken and from the time initial contact with the stricken individual is made by the emergency personnel involved. While systems of this type have proven highly beneficial, the benefits are not derived without certain attendant disadvantages. The initial disadvantage of systems of this type is that the dimensions of the stretcher are invariably increased beyond the standard ambulance stretcher dimensions, thus preventing use with standard ambulances and requiring special high ceiling ambulances. Such stretcher systems are not only increased in size in comparison with standard ambulance stretchers, but in total weight as well. Consequently, their movements to and from the ambulance are more restricted. Particularly in situations where access to the stricken individual requires movement of the stretcher up and down stairways, around restricted openings, etc., the ability to bring the treatment to the patient is lost and it becomes necessary to otherwise transport the patient to the nearest location to which the stretcher system can be conveniently moved.

An object of the present invention is the provision of a device which substantially eliminates the disadvantages of the stretcher systems heretofore noted while obtaining substantially all of the advantages thereof. In accordance with the principles of the present invention, this objective is obtained by providing a portable frame structure of a construction enabling the same to be manually carried to a patient position which is inaccessible in the sense previously noted above the conjunction with the discussion of the disadvantages of known stretcher systems. At the inaccessible patient location the frame structure is operable to be disposed in a patient supporting treatment and transportation position. Preferably, the frame structure is of collapsible construction, having parts relatively movable between a collapsed unit carrying position and the aforesaid patient supporting treatment and transportation position. Desirably, a frame structure presents a convenient carrying handle when in the aforesaid collapsed position enabling a single attendant to manually carry the frame structure together with the other treatment component parts thereof. Assist caster wheels may also for provided for use in carrying the unit.

The treatment components include a heart-lung resuscitator assembly and oxygen supply of the type previously permanently built into the aforesaid stretcher systems. In this way accessibility of this equipment to the patient is insured in situations where the patient had to be brought to the equipment heretofore in the operation of the stretcher systems as aforesaid. Moreover, the frame structure is provided with downwardly facing portions engageable with a horizontal surface such as a floor or the like to support the frame structure in stable relation thereon and thin mattress-like pad sections cooperable with the heart-lung resuscitator assembly to support a patient in supine relation. With this arrangement, the unit provides for a relatively unyielding support of the patient's back area sufficient to effect cardiac compression through the application of periodic mechanical downward forces on the chest area of the patient.

The heart-lung resuscitator assembly is of the type adapted to support the head of the patient in a position extending downwardly from the adjacent back area so that the breathing channel is maintained in a favorable position for the reception of oxygen. As previously stated, an oxygen supply is carried on the frame structure with suitable accessories to enable the supply to be directed to the patient.

The frame structure also provides a suitable handle portion disposed, when the frame structure is in the aforesaid patient supporting treatment and transporting position, at the head and foot ends thereof at positions manually engageable by two attendants stationed at such ends. Thus, the present unit not only enables the treatment to be brought to the patient at heretofore inaccessible positions, but enables the patient to be carried litter style from such position. Preferably, the heart-lung resuscitator assembly employed is power operated, such power deriving from the fluid pressure of the oxygen supply. This preferred arrangement enables continued treatment during transportation litter style in the unit.

It is of importance that the width dimension of the unit including the oxygen supply containers is of sufficient extent to provide the necessary back support for the application of the heart massage forces aforesaid but sufficiently limited to enable the unit to be supported on a conventional ambulance stretcher. This relationship secures several advantages in comparison with the known stretcher systems with built in heart-lung resuscitator assemblies. First, since the present unit is supportable on a conventional ambulance stretcher without increasing the dimensions thereof, all of the treatment advantages of the known stretcher systems can be obtained without the need to utilize a special raised ceiling ambulance as in the case otherwise as aforesaid. Moreover, by providing a separate unit having both treatment and transportation capabilities which cooperate with a conventional ambulance stretcher, the present availability and all-purpose advantages of a conventional ambulance stretcher are retained. Known stretcher systems embodying heart-lung resuscitator treatment functions are in practice generally restricted to use in emergency situations where such treatments are known to be needed. As previously stated where such capability is built into a stretcher system, its effectiveness for other uses is diminished to some extent. With the present invention the all-purpose efficiency and capability of the conventional ambulance stretcher is retained. The treatment function is provided to the full extent by the known stretcher systems and, in addition, beyond that, to situations of inaccessibility insofar as known stretcher systems are concerned.

The present invention also provides specific advantages in the specific construction features thereof. For example, the supine support provided the patient is with the legs slightly elevated. The construction providing this desirable support conveniently accommodates two separate oxygen supply containers and a conveniently accessible storage compartment for other treatment equipment such as drugs, supplies, heart monitoring units, defibrillators, etc. Likewise the unit provides a detachable mounting for an intravenous bottle support.

Another object of the present invention is the provision of a unit of the type described which is simple and light-weight in construction, effective in operation and economical to manufacture.

These and other objects of the present invention will become more apparent during the course of the following detailed description and appended claims.

The invention may best be understood with reference to the accompanying drawings wherein an illustrative embodiment is shown.

Figure 1:
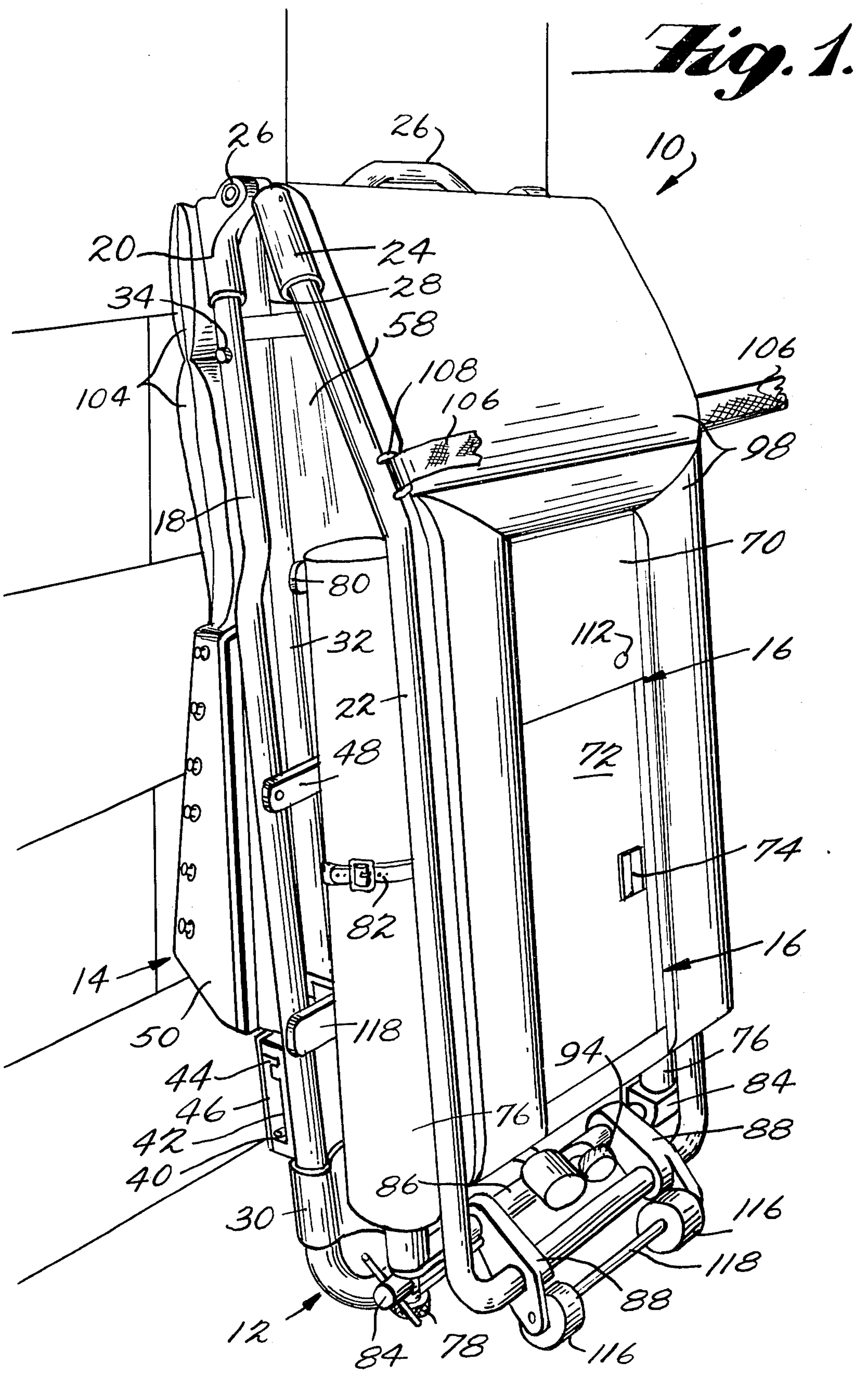
FIG. 1 is a perspective view of a device embodying the principles of the present invention showing the same in its collapsed carrying position.
Figure 2:
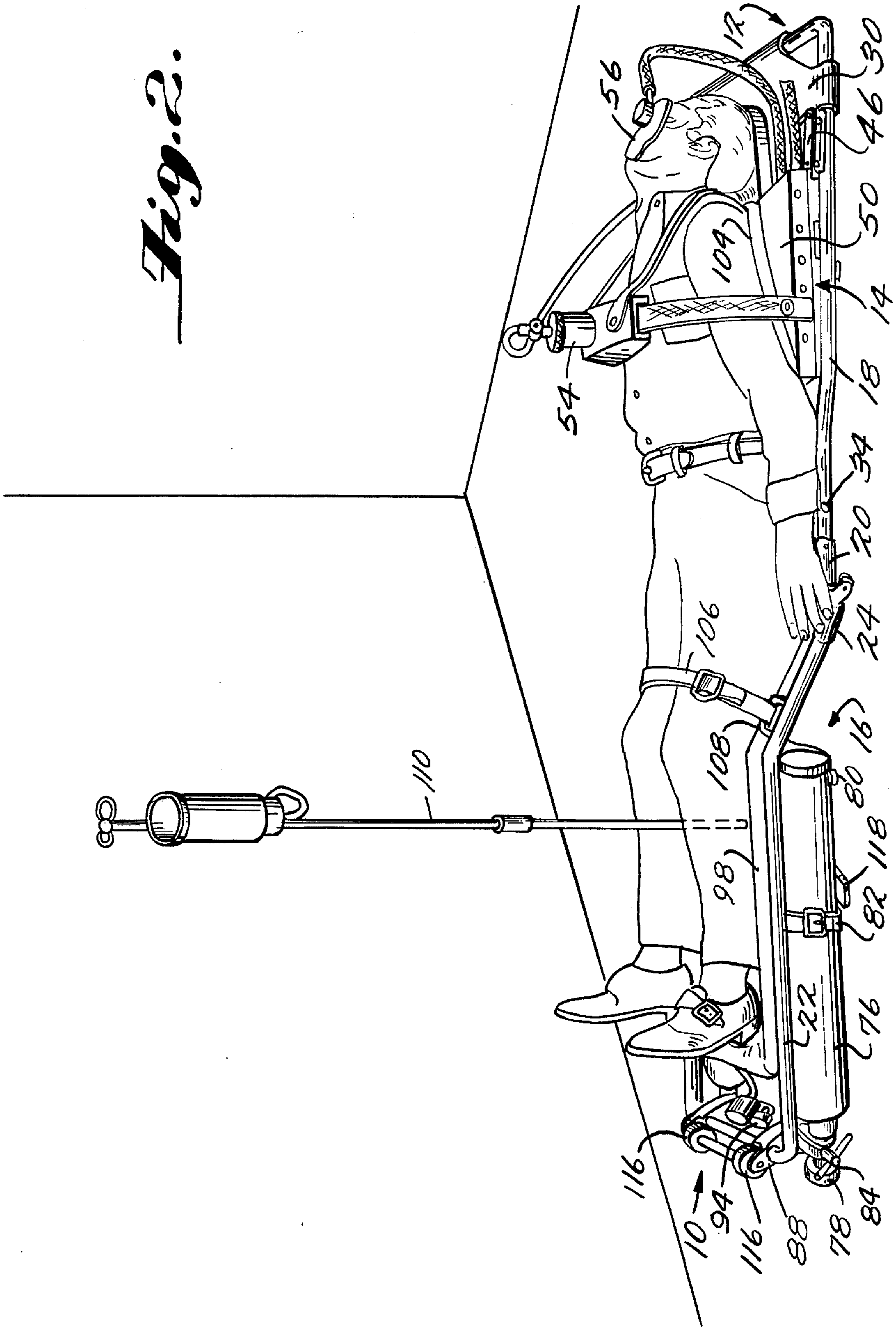
FIG. 2 is a perspective view of the device shown in FIG. 1 illustrating the same in its patient supporting treatment and transporting position.
Figure 3:
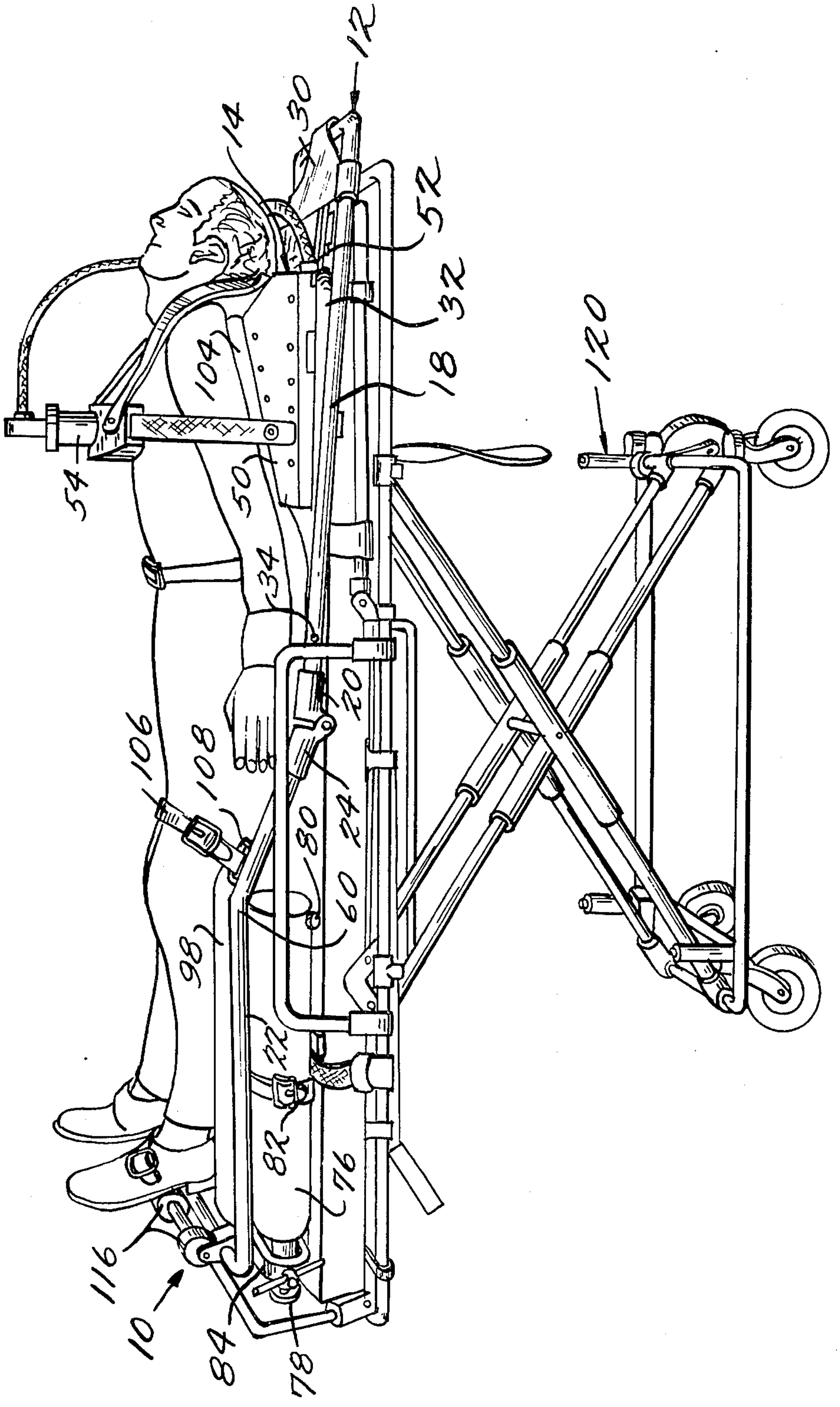
FIG. 3 is a perspective view of the device as shown in FIG. 2, illustrating the manner in which the device is supported on a conventional ambulance stretcher.

Referring now more particularly to the drawings, there is shown therein a device in the form of a heart-lung resuscitator litter unit, generally indicated at 10, which embodies the principles of the present invention. The unit 10 includes a frame structure, generally indicated at 12, which, as shown, is preferably constructed in two basic component parts pivotally interconnected together for movement between a collapsed storage and carrying position, as shown in FIG. 1, and an extended patient supporting treatment and transportation position, as shown in FIGS. 2 and 3.

Carried by the frame structure 12 and forming a portion of one component part thereof is a heart-lung resuscitator assembly, generally indicated at 14. Carried by the frame structure 12 and forming a portion of the other component part thereof is a storage compartment and oxygen container supporting assembly, generally indicated at 16.

The component part of the frame structure 12 which carries the heart-lung resuscitator assembly 14 is adapted to support the back area of the patient. While this component part of the frame structure may assume any desirable construction, the preferred embodiment illustrated in the drawings includes a main U-shaped tubular frame member 18 having a tubular pivotal fitting 20 fixed to the free end of each of its leg portions. The component part of the frame structure 12 which carries the assembly 16 is adapted to support the legs of the patient and the preferred embodiment illustrated in the drawings likewise includes a main U-shaped tubular frame member 22 having a pivotal fitting 24 fixed to the free end of each leg portion thereof. The pivotal fittings 20 and 24 are interconnected by a transversely extending rod 26, the ends of which serve as stub shafts for the pivotal fittings 20 and 24 and the center portion of which is bent upwardly to form a carrying handle portion.

Figure 4:
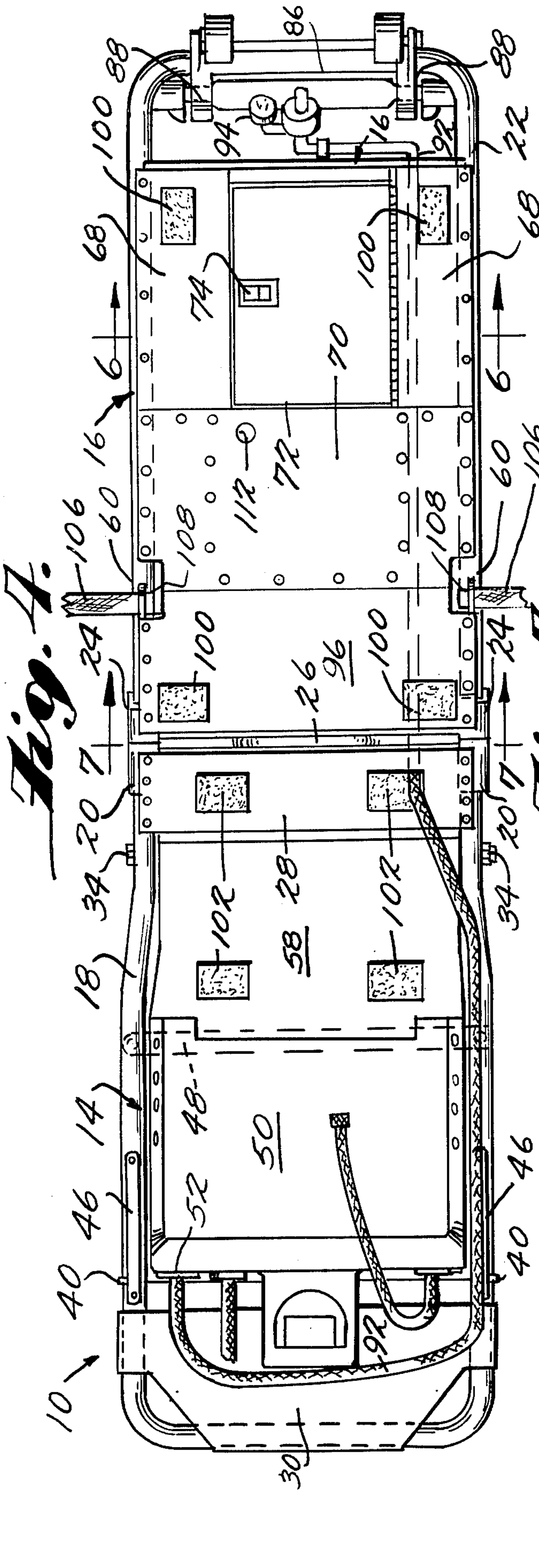
FIG. 4 is a top plan view of the device shown in FIG. 2 with the mattress-like pad sections and oxygen containers removed.

As can best be seen in FIG. 4, a plate 28 is suitably secured across the upper surfaces of the leg portions of the upper main frame member 18. A suitable connecting member 30 is similarly provided across the frame member 18 adjacent the bight portion thereof. As shown, the member 30 is preferably in the form of a canvas strap which is connected to the central bight portion of the frame member 28 as well as the adjacent leg portions. The members 28 and 30 form with the included leg portions of the main frame member a peripheral frame within which a sub-frame 32 is mounted for pivotal movement between raised and lowered positions. The sub-frame 32 may be of any suitable construction, the preferred embodiment shown being made up of angle iron elements welded into a U-shaped configuration. The ends of the legs of the U-shaped sub-frame 32 are pivoted within adjacent leg portions of the main frame member 18, as by pivot pins 34.

Figure 5:
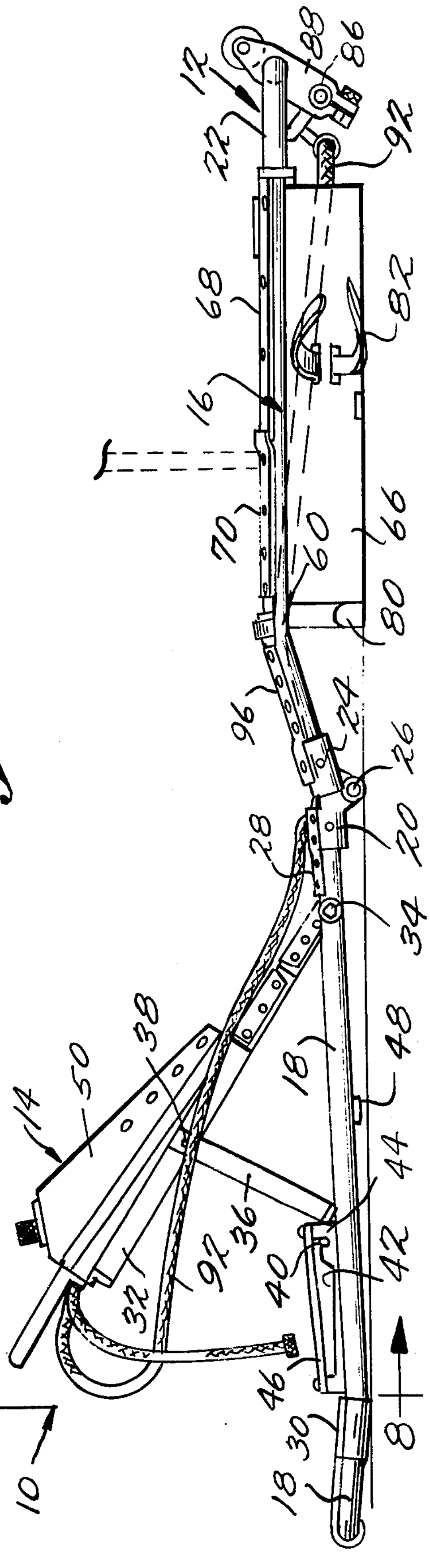
FIG. 5 is a side elevational view of the structure shown in FIG. 4 with the back section shown in raised position.

As best shown in FIG. 5, suitable means is provided for releasably retaining the sub-frame 32 in its raised position. As shown the preferred embodiment of such means includes a U-shaped strut member 36 having the free ends of its legs pivotally connected to the outer surfaces of the leg portions of the sub-frame 32 as indicated at 38. Extending outwardly from the legs of the strut 36 adjacent the bight portion thereof is a pair of pins 40 which are received within guide tracks 42 provided in track assemblies 44 suitably secured to the upper surface of the adjacent leg portions of the main frame member 18. As can be seen from FIG. 5, each of the tracks includes a notch portion 46 which receive the pins 40 when the strut member 36 is disposed in a position to support the sub-frame in its raised position. The strut is released by lifting upwardly thereon to move the pins out of the notches 46 enabling the pins to move toward the bight portion of the main frame 18, thus permitting the sub-frame 32 to move into its lowered position. A strap 48 is secured across the under surfaces of the leg portions of the main frame 18 to serve as a stop for the sub-frame 32 when the latter reaches its lowered position.

The heart-lung resuscitator assembly 14 is fixedly mounted on the sub-frame 32. The assembly may assume any conventional configuration. Preferably the assembl- is of the power actuated type, although it is within the contemplation of the present invention that manually actuated heart-lung resuscitator assemblies may be utilized. A specific example of the preferred heart-lung resuscitator assembly is disclosed in U.S. Pat. No. 3,511,275, the disclosure of which is hereby incorporated by reference into the present specification. Reference is also made to related U.S. Pats. Nos. 3,509,899; 3,551,052; and 3,307,541.

For purposes of obtaining a detailed understanding of the construction and operation of the heart-lung resuscitator assembly 14, reference can be had to the above-noted patents. For present purposes, it is sufficient to note that the assembly 14 includes a shoulder lift and head rest structure 50, an oxygen inlet 52, a cardiac compresser unit 54, and a lung ventilating unit 56 (see FIG. 2). The assembly 14 is suitably fixed to the upper surface of the sub-frame 32 at a position adjacent the bight portion thereof with the head rest of the structure 50 extending outwardly of the bight portion. In addition, a plate 58 is suitably fixed to the upper surface of the sub-frame adjacent the free ends of the leg portions 32 thereof.

Referring again to FIGS. 4 and 5, it will be noted that the main U-shaped frame member 22 of the lower component part of the frame structure 12 has the free end sections of the leg portions thereof formed with angular bends 60 which serve to slightly elevate the remaining leg portions and bight portion above the upper main frame member 18 when the frame structure 12 is in its operative position. The storage compartment and oxygen container supporting assembly 16 is fixed to the upper surface of the elevated sections of the leg portions of the frame member 22 so that the storage compartment of the assembly 16 is positioned centrally therebelow and the supports for the oxygen containers are at positions on opposite sides of the compartment at the same level. While the assembly 16 may assume any suitable construction, in the preferred embodiment shown the compartment is formed by a bent sheet metal structure which provides a compartment defined by a bottom 62, two end walls 64 and two side walls 66 and attaching flanges 68 extending horizontally outwardly from the side walls 64. The portions of the flanges 68 extending toward the bight portion of the frame member 22 extend outwardly a distance sufficient to engage over the leg portions of the member 22 where they are affixed thereto by suitable fasteners. The remaining portions of the flanges 68 are of lesser outward extent and serve as an attaching structure for a cover plate 70. As best shown in FIG. 4, the cover plate 70 is suitably fixed to the contiguous portions of the flanges 68 and extend outwardly over the contiguous leg portions of the frame 22 where suitable fasteners are provided to effect securement. The compartment of the assembly 16 includes a hinged door 72 suitably releasably latched, as indicated at 74, into a closed position for upward swinging movement into an opened position.

The oxygen container supporting means of the assembly 16 may be of any suitable construction. With reference to FIGS. 1–3, it will be noted that the oxygen containers themselves are of the cylinder type, as indicated at 76, having a manually actuated valved outlet formed in a necked down portion at one end thereof. A valve actuating handle 78 is removably mounted on the valve stem in concentric relation to the cylindrical axis and the outlet extends radially outwardly therefrom. It will be understood that the containers as described above are of conventional design and, of course, any other appropriate design may be utilized.

The supporting means for each cylinder 76 includes a generally J-shaped metal support strap 80 secured to the associated compartment side wall 66 in a position to engage beneath the end of the cylinder remote from the valve handle 78. A flexible buckled strap 82 is extended through appropriate openings in the central portion of the associated side wall 66 to secure the central portion of the cylinder 76 thereto. The necked-down end of each cylinder 76 is received within a clamp 84 (as by removing handle 78) fixed to the exterior end of a manifold tube 86. The manifold tube 86 is, in turn, fixedly attached to the frame structure 12 by a pair of laterally spaced brackets 88 fixed to the bight portion of the frame member 22. The ends of the manifold tube 86 are arranged to sealingly receive the lateral outlet of the cylinders 76 when engaged therein and the clamps 84 serve to firmly maintain such engagement. With this arrangement the pressurized oxygen within either cylinder 76 can be communicated with the manifold tube 86 simply by turning the valve handle 78 thereof in a direction to open the control valve.

The central portion of the manifold tube 86 has an outlet 90 communicating therewith to which one end of a flexible conduit or hose 92 is connected. A suitable pressure gauge 94 can be operatively associated with the outlet 90, if desired. As best shown in FIG. 4, the hose 92 is extended along the length of the frame structure 12 and has its opposite end connected with the inlet 52 of the heart-lung resuscitator assembly 14.

It will be noted that the angular extremities of the leg portions of the main frame 22 have a plate 96 secured to the upper surfaces thereof. The upper surface of the plate 96 along with the upper surfaces of the longer portions of the flanges 68 and plate 70 are adapted to receive a generally U-shaped thin mattress-like pad 98 (see FIG. 1) which serves to support the lower portion of the patient. The pad 98 is retained in position by any suitable means such as cooperating Velcro fastener strips as indicated at 100 in FIG. 4. Similar strips 102 are provided on the plates 28 and 58 for maintaining a similar pad 104 on the upper surfaces thereof. The pad 104 is shaped to also extend over the upper surfaces of the shoulder lift and head rest structure 50 as well.

It will be noted that the heart-lung resuscitator assembly 12 provides straps to hold the upper portion of the patient on the pad 104. Straps 106 are connected to the bends 60 of member 22 as by hooks 108, for the purpose of holding the lower portion of the patient on the pad 98.

Figure 6:
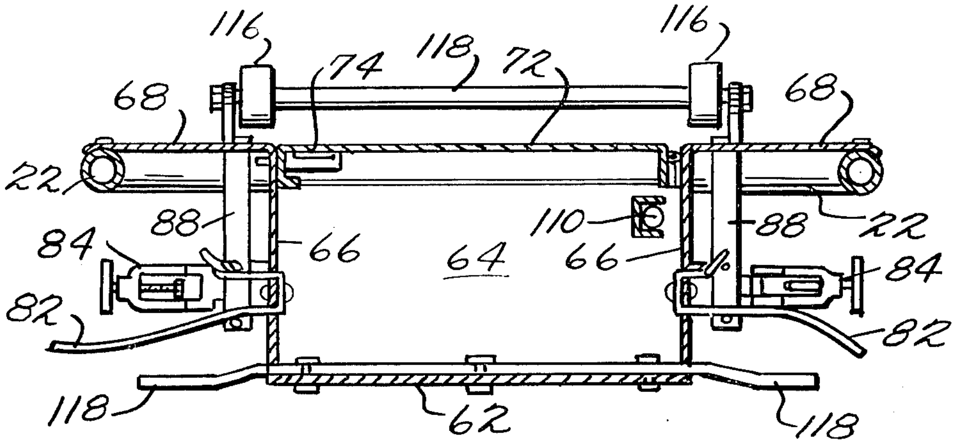
FIG. 6 is an enlarged fragmentary sectional view taken along the lines 6—6 of FIG. 4.
Figure 7:
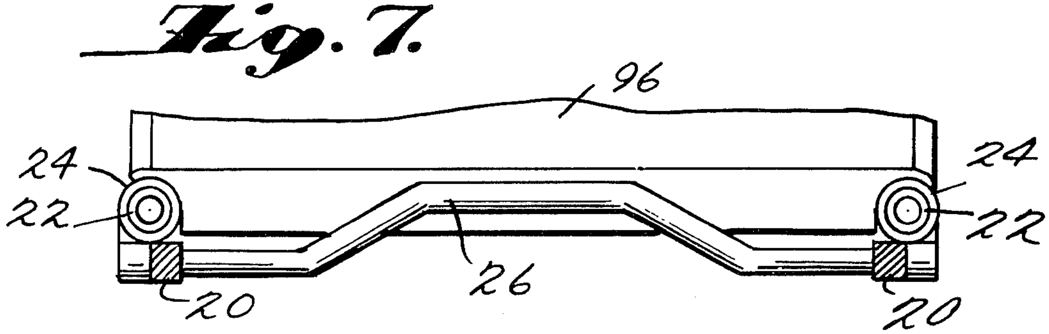
FIG. 7 is an enlarged fragmentary sectional view taken along the lines 7—7 of FIG. 4.
Figure 8:
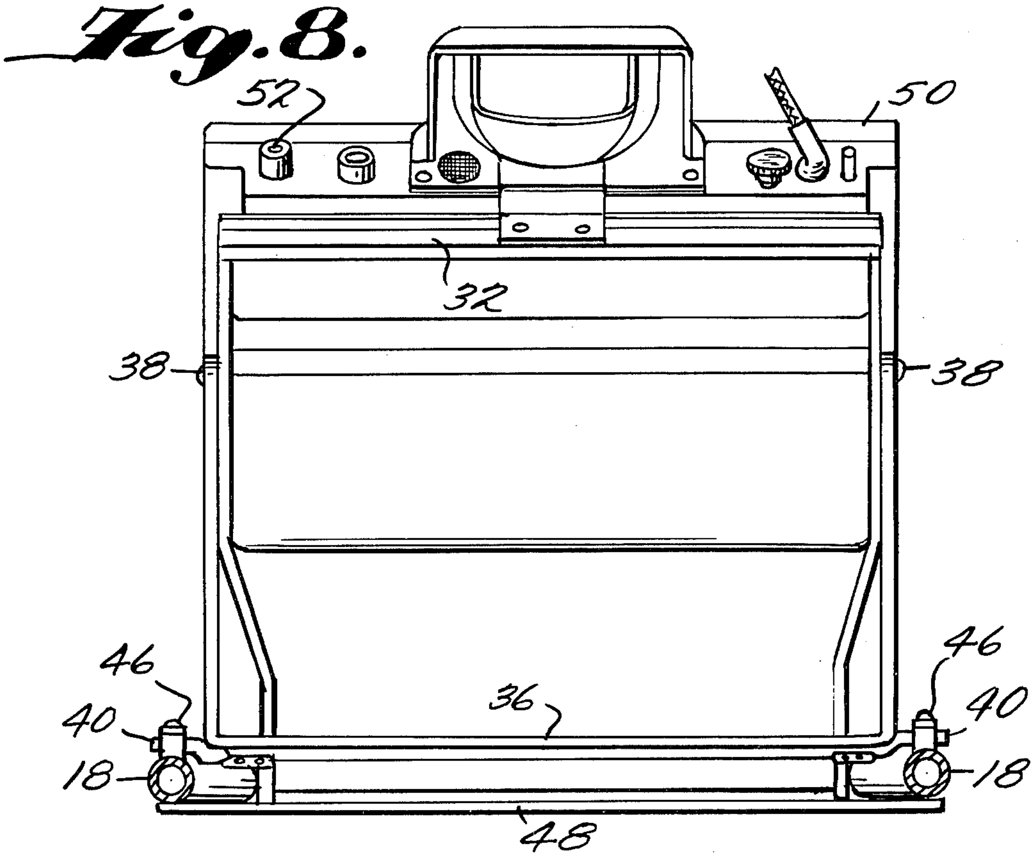
FIG. 8 is an enlarged fragmentary sectional view taken along the lines 8—8 of FIG. 5.

The assembly 16 also provides a means for storing a telescopic pole assembly 110, as in the compartment provided thereby (see FIG. 6), and for mounting the pole assembly 10 in an operative position where it can support a bottle or other container for a fluid to be supplied intravenously to the patient (see FIG. 2). The support of the pole assembly 110 is by means of an opening 112 in the plate 70 (see FIG. 4) and a socket structure (not shown) in the compartment therebelow.

The unit 10 also includes a pair of wheels 114 which are mounted on a shaft 116 supported in brackets 88. Finally, a laterally extending stop plate 118 is provided in the assembly 16 (see FIG. 6) for engaging the leg portions of frame member 18 when the frame structure is in its collapsed position as shown in FIG. 1.

As previously indicated, the collapsable and and extendable frame structure 12 provides the unit 10 with the capability of being moved easily and conveniently between a collapsed storage and carrying position, as shown in FIG. 1 and an extended patient supporting treatment and transportation position, as shown in FIGS. 2 and 3. This capability is provided through the simple expedient of a single pivot which also serves as a handle for carrying the unit in its collapsed position or in moving the unit on the wheels 116 when in its collapsed position. A commercial embodiment of the present invention weighs less than 50 pounds (without the oxygen container 76). This minimum weight enables the unit to be readily moved in its collapsed position direction to the emergency site, through pathways which could not be reached by a conventional ambulance stretcher, due to the size thereof. The dimensions of the unit in its collapsed position are approximately 42 inches by 22 inches by 13 inches.

Once the unit has been transported to the emergency site, the frame structure 12 is readily moved from its collapsed position into its extended patient supporting treatment and transportation position, as shown in FIGS. 2 and 3. In this position the aforesaid commercial embodiment has a size of approximately 78 inches by 19 inches by 6⅝ inches. This is adequate size to support patients of normal size and above in the position clearly shown in FIG. 2. It will be noted that in this position the patient is supported in a highly advantageous manner for receiving treatment such as heart-lung resuscitation, intravenous feeding, and the like. By utilizing a heart-lung resuscitator assembly of the type previously noted, all of the advantages inherent in this type of assembly are obtained in the present unit. Moreover, the unit itself supports the oxygen containers in the form of two E size cylinders 76 so that it is not necessary to provide for separate support of the cylinders. The arrangement of the cylinders in the unit is particularly advantageous in terms of the conservation of space afforded. Moreover, the unit further provides for a drug and equipment compartment which, in the commercial embodiment, has dimensions of 5½ inches deep, 9⅝ inches wide, and 24 inches long, which is equal to approximately 1,181 cubic inches. This space is quite adequate for storing telescopic I.V. pole 110, telemetry ECG monitoring equipment, ECG encoder for remote ECG analysis, as well as a suitable supply of drugs and other equipment utilized in conjunction with emergency treatment. The assembly 16 which provides the compartment and serves to support the oxygen containers (which may be E-size cylinders) insures that adequate equipment will be available in a unitized fashion for use in emergency situations.

The unit 10 of the present invention is particularly suited for use with ambulances and mobile intensive care units. In this regard, it will be understood that the above-recited dimensions of the unit when in its patient supporting position permits the unit to be bodily lowered onto a conventional ambulance stretcher, as is clearly illustrated in FIG. 3. FIG. 3 illustrates an ambulance stretcher 120, the details of construction of which can be obtained by referring to U.S. Pat. No. 3,644,944, the disclosure of which is hereby incorporated by reference into the present specification. It will be understood that in transporting the litter unit from the position of initial emergency to the stretcher 120, the bight portions of the frames 18 and 22 are utilized as hand grips for the two individuals which would serve to transport or carry the unit from the place of emergency to the stretcher. The present unit is also capable of being utilized with hospital emergency carts. Another appropriate use of the unit 10 is at large industrial plants, airports, stadiums, golf courses, resorts, large office buildings, or wherever there are a large number of people and mobility is required. The unit may be utilized with especially built vehicles similar to those of the golf cart variety for transportation in such large installations in lieu of hand carrying.

It thus will be seen that the objects of this invention have been fully and effectively accomplished It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. A device for use under emergency conditions in applying heart-lung resuscitation procedures and the like to a patient while supported thereon which enables such patient to be transported from an inaccessible location of attack onto an ambulance stretcher without removing such support, said device being in the form of a self-contained portable unit, said unit comprising:

a frame structure having a first part for supporting the legs and a second part for supporting the back of a patient, means connecting said parts for movement between a collapsed unit carrying position and an extended patient supporting treatment and transporting position, downwardly facing horizontal surface engaging means on said first and second parts of said frame structure operable when said frame structure is disposed in said patient treatment and transporting position to engage a horizontal surface such as a floor or the like and support said frame structure in stable relation thereon, said parts including upwardly facing patient engaging means on said frame structure operable when said frame structure is disposed in said patient treatment and transporting position to engage and support a patient on said frame structure in a supine position and cooperating with said horizontal surface to provide for a relatively unyielding support of the patient's back area sufficient to effect cardiac compression through the application of periodic mechanical downward forces on the chest area of the patient, means carried by said frame structure on said second part for applying said periodic mechanical downward forces on the chest area of the patient when said patient engaging means and said horizontal surface engaging means are in cooperating relation as aforesaid, said upwardly facing patient engaging means on said second part being contoured adjacent the head end of said frame structure to support the head of the patient in a position extending downwardly from the adjacent back area so that the breathing channel is maintained in a favorable position for the reception of oxygen, storage compartment means carried by said frame structure on said first part thereof in a position generally below the level of the associated patient engaging means when said frame structure is disposed in said patient supporting position so as to define a space for the reception of suitable emergency treatment supplies which is conveniently accessible, oxygen tank supporting means carried by said frame structure on said first part for supporting a pair of oxygen cylinders in a position generally below the level of the associated patient engaging means alongside said storage compartment means, the downwardly facing horizontal surface engaging means of said first and second parts and the leg supporting portions of the upwardly facing patient engaging means on said first part when in said patient supporting position being disposed in generally parallel planes spaced apart a distance generally equal to the vertical height of the space defined by said storage compartment means, means carried by said frame structure engageable with a patient supported as aforesaid for supplying oxygen from said container means to the patient, manually engageable means at the head and foot ends of said frame structure for enabling two attendants stationed at said ends to lift and carry said unit and a patient supported on said frame structure as aforesaid by manual engagement of said manually engageable means, the width dimensions of said unit with oxygen container means supported thereon when in supporting relation to a patient being sufficiently extended to provide the aforesaid back area support but sufficiently limited to enable the unit to be supported on a conventional ambulance stretcher, and said horizontal surface engaging means of said first and second parts when said frame structure is in said collapsed position being disposed in adjacent relation so that with oxygen container means supported on the unit the latter is of a size and shape to enable movement thereof by one attendant to an inaccessible location of attack.

2. A device as defined in claim 1 wherein said parts are of generally similar rectangular configuration in plan and said connecting means comprises a pivoted connection interconnecting said parts in end-to-end relation for pivotal movement about a transverse axis between said collapsed and patient supporting positions.

3. a device as defined in claim 1 wherein said periodic force applying means comprises a heart-lung resuscitator assembly operable to automatically apply said periodic forces in response to the application of fluid pressure thereto supplied by the oxygen in the aforesaid container means when operatively engaged with a patient supported in said supine position on said patient engaging means.

4. A device as defined in claim 3 including means carried by said frame structure for selectively supplying oxygen from one of two oxygen containers constituting the container means.

5. A device as defined in claim 1 wherein the upwardly facing patient engaging means adjacent the head end of said frame structure is carried by a sub-frame mounted on said frame structure for movement between raised and lowered positions, and means for releasably holding said sub-frame in said raised position whereby the patient is supported with the head elevated and the trunk inclined upwardly.

6. A device for use under emergency conditions in applying heart-lung resuscitation procedures and the like to a patient while supported thereon which enables such patient to be transported from an inaccessible location of attack onto an ambulance stretcher without removing such support, said device being in the form of a self-contained portable unit, said unit comprising:

a frame structure having parts relatively movable between a collapsed unit carrying position and an extended patient supporting treatment and transporting position, said frame structure including two parts of generally similar rectangular configuration in plan interconnected in end-to-end relation for pivotal movement about a transverse axis between said collapsed and patient supporting positions, downwardly facing horizontal surface engaging means on said frame structure operable when said frame structure is disposed in said patient treatment and transporting position to engage a horizontal surface such as a floor or the like and support said frame structure in stable relation thereon, upwardly facing patient engaging means on said frame structure operable when said frame structure is disposed in said patient treatment and transporting position to engage and support a patient on said frame structure in a supine position and cooperating with said horizontal surface engaging means when the latter is engaged upon a horizontal surface to provide for a relatively unyielding support of the patient's back area sufficient to effect cardiac compression through the application of periodic mechanical downward forces on the chest area of the patient, means carried by said frame structure for applying said periodic mechanical downward forces on the chest area of the patient when said patient engaging means and said horizontal surface engaging means are in cooperating relation as aforesaid, said upwardly facing patient engaging means being contoured adjacent the head end of said frame structure to support the head of the patient in a position extending downwardly from the adjacent back area so that the breathing channel is maintained in a favorable position for the reception of oxygen, storage compartment means carried by said frame stucture on a leg supporting part thereof in a position generally below the level of the associated patient engaging means when said frame structure is disposed in said patient supporting position so as to define a space for the reception of suitable emergency treatment supplies which is conveniently accessible, oxygen tank supporting means carried by said frame structure on said leg supporting part for supporting a pair of oxygen cylinders in a position generally below the level of the associated patient engaging means alongside said storage compartment means, face mask means carried by said frame structure engageable with the face of a patient supported as aforesaid for supplying oxygen from said container means to the patient, manually engageable means at the head and foot ends of said frame structure for enabling two attendants stationed at said ends to lift and carry said unit and a patient supported on said frame structure as foresaid by manual engagement of said manually engageable means, the width dimensions of said unit with oxygen container means supported thereon when in supporting relation to a patient being sufficiently extended to provide the aforesaid back area support but sufficiently limited to enable the unit to be supported on a conventional ambulance stretcher, and said unit when said frame structure is in said collapsed position with oxygen container means supported thereon being of a size and shape to enable movement thereof by one attendant to an inaccessible location of attack, one of said frame structure parts constituting a patient leg supporting part, said patient leg supporting part including a central storage compartment assembly having a closable access opening facing upwardly when said frame structure is disposed in said patient supporting position, said patient engaging means including patient leg supporting pad portions on opposite sides of said storage compartment assembly, said oxygen container means supporting means comprising a pair of cooperative supporting assemblies each being operable to support a separate elongated cylindrical oxygen container adjacent one side of said compartment assembly and beneath the associated pad portion when said frame structure is in said patient supporting position.

7. A device as defined in claim 6 wherein one of said parts includes a central handle located at the pivotally interconnected end thereof, said handle being generally overlaid by said patient engaging means when said frame structure is in said patient supporting position, said handle extending upwardly in exposed relation when said frame structure is in said collapsed position.

8. A device as defined in claim 7 wherein at least one of said parts has roller means mounted on the free end thereof ground engageable when said frame structure is in said collapsed position.

* * * * *